United States Patent [19]

Umemura et al.

[11] 4,264,476
[45] Apr. 28, 1981

[54] CATALYST FOR PRODUCING ACRYLONITRILE IN A FLUIDIZED BED REACTOR

[75] Inventors: Sumio Umemura; Kyoji Ohdan; Mikio Hidaka; Toshio Kurafuji, all of Ube, Japan

[73] Assignee: UBE Industries, Inc., Yamaguchi, Japan

[21] Appl. No.: 85,708

[22] Filed: Oct. 17, 1979

[30] Foreign Application Priority Data

Oct. 20, 1978 [JP] Japan .................. 53/128406

[51] Int. Cl.$^3$ .................. B01J 29/00; B01J 27/02; B01J 29/16; B01J 29/10
[52] U.S. Cl. .................. 252/458; 252/439; 252/456; 252/459
[58] Field of Search .................. 252/439, 458

[56] References Cited

U.S. PATENT DOCUMENTS

| | | | |
|---|---|---|---|
| 3,766,092 | 10/1973 | Honda et al. | 252/437 |
| 3,890,248 | 6/1975 | Ohara et al. | 252/458 X |
| 3,907,713 | 9/1975 | Grasselli et al. | 252/458 X |
| 3,954,856 | 5/1976 | Kobayashi et al. | 252/439 X |
| 4,034,008 | 7/1977 | Kurtz et al. | 252/458 X |
| 4,035,418 | 7/1977 | Okada et al. | 252/439 X |
| 4,097,518 | 6/1978 | Umemura et al. | 252/458 X |

FOREIGN PATENT DOCUMENTS

| | | |
|---|---|---|
| 1319190 | 6/1973 | United Kingdom . |
| 1330074 | 9/1973 | United Kingdom . |
| 1478621 | 7/1977 | United Kingdom . |

Primary Examiner—Delbert E. Gantz
Assistant Examiner—William G. Wright
Attorney, Agent, or Firm—Miller & Prestia

[57] ABSTRACT

An improved catalyst suitable for use in the production of acrylonitrile by the catalytic ammoxidation of propylene in a fluidized bed reactor is provided. This catalyst contains 40 to 60% by weight of silica, in terms of $SiO_2$, and 60 to 40% by weight of a composition having the formula:

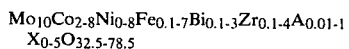

$$Mo_{10}Co_{2-8}Ni_{0.1-7}Fe_{0.1-7}Bi_{0.1-3}Zr_{0.1-4}A_{0.01-1}X_{0.5}O_{32.5-78.5}$$

wherein A is the alkali metals, X is Ti, Te, V, Mn, Cr, W and/or Sn, provided that the total number of Co and Ni atoms is 2 to 10, and has 150 to 500 Å of the average pore radius, 0.2 to 0.5 $cm^3/g$ of the total pore volume and 30 to 60 $m^2/g$ of the specific surface area. This catalyst has an improved attrition resistance and acrylonitrile can be produced, in the presence of this catalyst, at a high yield by the ammoxidation reaction of propylene in a fluidized bed reactor.

5 Claims, No Drawings

CATALYST FOR PRODUCING ACRYLONITRILE IN A FLUIDIZED BED REACTOR

FIELD OF THE INVENTION

The present invention relates to an improved catalyst for producing acrylonitrile by the catalytic ammoxidation of propylene in a fluidized bed reactor. More specifically, it relates to an improved catalyst for producing acrlyonitrile in a fluidized bed reactor, which catalyst has an improved attrition resistance and is capable of producing acrylonitrile at a high yield.

DESCRIPTION OF THE PRIOR ART

Heretofore, various methods for producing acrylonitrile by the catalytic ammoxidation of propylene in, for example, fixed bed reactors, fluidized bed reactors and the like have been well known in the art. Many kinds of conventional catalysts, which are used in the production of acrylonitrile by the catalytic ammoxidation, were proposed, after bismuth phosphorus molybdate (P—Mo—Bi—O) type catalysts were proposed in U.S. Pat. No. 2,904,580.

Proposed were, for example, Mo—Bi—Fe—Co—Na,K—P—O type catalysts in U.S. Pat. No. 3,766,092, Mo—Bi—Fe—+P.As+—Ni,Co—+the alkali metals, Ta, Nb, the rare earth metals+—O type catalysts in G.B. No. 1,319,190, (the alkali metals)—(Ni,Co)—(P.As) (the element belonging to IIa and IIb Groups of the Periodic Table)+—Fe—Bi—Mo—O type catalysts in G.B. No. 1,330,074, Ge, Sn, Cu, Ag, Cr, Ru, Ti, W, Be, B, Ga, In, Mn, Sb, Th, Zr, Y—the alkali metals—Ni,Co—Fe—Bi—Mo—O type catalysts in G.B. No. 1,478,621 and the like.

However, in the case where the catalytic ammoxidation of propylene is carried out in a fluidized bed reactor by using a known catalyst, attrition loss of the catalyst particles is remarkably high and also the acrylonitrile yield is far less than that obtained in a fixed bed reactor. Particularly, catalysts containing, as essential ingredients, molybdenum and bismuth have the problems in that not only do the activity and the selectivity of the catalysts become worse due to the sublimation loss of the molybdenum during the ammoxidation reaction, but also the attrition resistance of the catalysts is remarkably impaired and the life of the catalysts is short due to the facts that the properties of the catalysts are changed with the lapse of time and the particles of the catalysts are expanded.

Although certain catalysts containing, as essential ingredients, molibdenum, bismuth, iron and cobalt (or nickel) exhibit a relatively high acrylonitrile yield, the attrition properties of the particles of the catalysts and the acrylonitrile yield are not sufficient for practical use when they are used in a fluidized bed reactor. In addition, there are problems in these catalysts that a relatively high reaction temperature and a relatively long contact time are required.

Catalysts having an improved attrition property such as those containing antimony or those containing tungsten together with iron, cobalt, nickel, manganese and the like have also been proposed. However, these catalysts do not afford a satisfactory acrylonitrile yield when they are used in the ammoxidation of propylene in a fluidized bed reactor.

SUMMARY OF THE INVENTION

Accordingly, the main objects of the present invention are to obviate the aforementioned problems of the conventional catalysts used in the ammoxidation of propylene and to provide a catalyst which is capable of producing acrylonitrile at a high yield under the conditions of a relatively low reaction temperature and a relatively short contact time and which has an improved attrition resistance when the catalyst is used in the ammoxidation of propylene in a fluidized bed reactor.

Other objects and advantages of the present invention will be apparent from the following description.

In accordance with the present invention there is provided a catalyst containing molybdenum, cobalt, iron, bismuth, zirconium, the alkali metals and oxygen supported on a carrier which is used for producing acrylonitrile by the catalytical ammoxidation of propylene in a fluidized bed reactor wherein the catalyst comprises 40 to 60% by weight (preferably, 45 to 55% by weight), in terms of $SiO_2$, of silica and 60 to 40% by weight (preferably, 55 to 45% by weight) of an oxide composition having the formula:

$$Mo_aCo_bNi_cFe_dBi_eZr_fA_gX_hO_j \qquad [I]$$

wherein Mo is molybdenum, Co is cobalt, Ni is nickel, Fe is iron, Bi is bismuth, Zr is zirconium, A is the alkali metals, preferably at least one alkali metal selected from the group consisting of potassium, rubidium and cesium, X is at least one element selected from the group consisting of titanium, tellurium, vanadium, manganese, chromium, tungsten and tin and O is oxygen; the subscripts a, b, c, d, e, f, g, h and j represent the number of atoms in the catalyst and, when a is 10, b is 2 to 8 (preferably 4 to 7) and c is 0 to 8 (preferably 0 to 7), provided that b+c is 2 to 10 (preferably 4 to 7), d is 0.1 to 7 (preferably 0.5 to 3), e is 0.1 to 3 (preferably 0.5 to 2), f is 0.1 to 4 (preferably 0.15 to 2), g is 0.01 to 1 (preferably 0.03 to 0.3), h is 0 to 5 (preferably 0 to 2) and j is the number which is required by the total valence of the other elements except for oxygen and is generally 32.5 to 78.5, and has micro pores on the surface thereof, the average pore radius being 150 to 500 Å (preferably 200 to 400 Å) and the total pore volume being 0.2 to 0.5 $cm^3/g$ (preferably 0.3 to 0.45 $cm^3/g$) and the specific surface area of the catalyst being 30 to 60 $m^2/g$ (preferably 35 to 55 $m^2/g$).

DESCRIPTION OF THE INVENTION

The "average pore radius" and "total pore volume" used herein are measured as follows: 0.5 g of a sample (catalyst) is put into a dilatometer. After the dilatometer is evacuated to $2\times10^{-2}$ mmHg or less by a vacuum pump, mercury is introduced into the dilatometer and, then, the dilatometer is charged in an autoclave. The autoclave is gradually pressurized from an atmospheric pressure up to 1500 $kg/cm^2$ (gauge pressure) and the decrease in the level of the mercury is continuously monitored. From the correlation between the pressure change and the level change of the mercury (i.e. the decrease in the volume of the mercury), the pore distribution is measured and, thus, the average pore radius and the total pore volume are determined (mercury pressure porosimeter).

The specific surface area (m²/g) of the catalyst used herein is determined according to the BET method based on nitrogen gas adsorption.

The proportion of each element constituting the catalyst of the present invention (i.e. the composition of the catalyst), the average pore radius, the total pore volume and the specific surface area of the catalyst are important factors in the present invention. If one of these factors is out of the range set forth above, the aforementioned objects of the present invention cannot be accomplished. For instance, if the number (b) of the cobalt (Co) atoms in the formula [I] is more than 8 when the number (a) of the molybdenum (Mo) atoms is 10, the selectivity to the acrylonitrile is low and the attrition resistance of the catalyst becomes worse. On the other hand, if the number (b) of the cobalt atoms is less than 2 when a=10, the selectivity to the acrylonitrile and the conversion of the propylene are low. Although nickel (Ni) can be contained together with cobalt (Co) in the present catalyst, the total number (b+c) of the cobalt and the nickel atoms should be within the range of from 2 to 10 (when a=10). If b+c is less than 2, the conversion of the propylene is low. On the other hand, if b+c is more than 10, the selectivity to the acrylonitrile is low.

Although the attrition resistance of the catalyst is not adversely affected by the number (d) of the iron atoms in the formula [I], both the conversion of the propylene and the selectivity to the acrylonitrile are low when the number (d) of the iron atoms is out of the range of 0.1 to 7 when a=10. Especially, if d is less than 0.1, the selectivity to the acrylonitrile remarkably decreases. On the other hand, if d is more than 7, the conversion of the propylene remarkably decreases. If the number (e) of the bismuth (Bi) atoms in the formula [I] is less than 0.1 (when a=10), the conversion of the propylene tends to decrease although the attrition resistance of the catalyst is not adversely affected. On the other hand, if e is more than 3, not only do the selectivity and yield of the acrylonitrile decrease but also the attrition resistance of the catalyst remarkably decreases. Thus, the properties of the slurry, containing the constituent elements of the catalyst, in the catalyst preparation step (from which slurry the present catalyst if prepared, for example, by spray drying technique) are not suitable for spray drying.

If the number (f) of the zirconium (Zr) atoms in the formula [I] is less than 0.1 or more than 4 (when a=10), the selectivity to the acrylonitrile is particularly low and the acrylonitrile yield is also low. If the number (g) of the alkali metal (A) atoms in the formula [I] is less than 0.01 (when a=10), the selectivity to the acrylonitrile somewhat decreases. On the other hand, if g is more than 1, although the selectivity to the acrylonitrile increases, (i) the acrylonitrile yield becomes worse due to the decrease in the conversion of the propylene, (ii) the attrition resistance of the catalyst decreases, and (iii) the amount of the by-product (i.e. acrolein) increases.

If the number (h) of the atoms of the component X (i.e. titanium, tellurium, vanadium, manganese, chromium, tungsten and/or tin) is more than 5 (when a=10), the attrition resistance and the acrylonitrile yield are generally low. The component X can be used alone or in any combination with the above-mentioned elements.

Even though a catalyst has the composition shown in the formula [I], if the average pore diameter, the total pore volume and/or the specific surface area of the catalyst are out of the range specified above, it is difficult to accomplish the objects of the present invention due to a decrease in the conversion of the propylene, the selectivity to the acrylonitrile and/or the attrition resistance of the catalyst. In addition, when the content of the silica, in terms of $SiO_2$, in the catalyst is less than 40% by weight, sufficient attrition resistance can not be obtained. On the other hand, when the content of the silica is more than 60% by weight, the conversion of the propylene and the selectivity to the acrylonitrile, especially the selectivity to the acrylonitrile, unpreferably decrease.

The catalyst of the present invention suitable for use in the production of acrylonitrile in a fluidized bed reactor can be prepared, for example, in the following manner.

Silica sol and compounds containing the constituent elements of formula [I] are mixed with each other in an aqueous medium at a temperature of 30° to 70° C., preferably 40° to 60° C. in such an amount that the catalyst comprises 40 to 60% by weight of silica, in terms of $SiO_2$ and 60 to 40% by weight of the composition of formula [I]. Thus, a slurry having a temperature within the above-mentioned range and having a pH of not more than 4, preferably not more than 2, is prepared. The slurry is spray dried to form fine particles having an average size of, preferably, 40 to 80 microns, more preferably 50 to 70 microns and, then, the spray dried particles are calcinated at a temperature of 500° to 700° C., preferably 550° to 650° C. under an atmosphere of an oxygen-containing gas for, generally, 1 to 30 hours and, preferably, 5 to 15 hours. Thus, the desired catalyst having micro pores on the surface thereof is obtained. The spray drying and calcination steps are not critical to the present invention, and any conventional equipment and technique can be employed in the preparation of the catalyst of the present invention.

The compounds containing the constituent elements of formula [I] that can be employed in the catalyst preparation process mentioned above, include, for example, salts such as nitrate, ammonium salt, carbonate, organic acid salts, hydrochloride of each constituent element of formula [I] and oxides of the constituent elements. In order to prepare a slurry having properties suitable for the spray drying, it is preferable to use compounds that are soluble in water, nitric acid, aqueous ammonia, and, more preferably, compounds that are also heat degradable during the calcination step. Example of such preferable compounds are, for example, nitrates, ammonium salts and the like, such as ammonium molybdate, cobalt nitrate, nickel nitrate, ferric nitrate, potassium nitrate, rubidium nitrate, cesium nitrate, zirconium oxide nitrate, manganese nitrate, chromium nitrate, ammonium metavanadate, ammonium paratungstate. These compounds containing the constituent elements of the present catalyst are preferably employed in the form of a solution of water, nitric acid, aqueous ammonia or the like in the preparation process of the catalyst.

The order in which the compounds containing the constituent elements of the catalyst (preferably in the form of a solution) and the silica sol are added to each other is not critical. However, it is preferable to add the silica sol to a solution of a compound containing any constituent element of the catalyst or any mixture of the solution which has previously been adjusted to a pH of not more than 4 and, preferably, of not more than 2. If the pH is too high when the silica sol is added to the solution, the slurry so prepared is not suitable for the spray drying due to the generation of coagulated particles in the slurry.

In the catalyst preparation process mentioned above, if the mixing temperature of the ingredients is less than 30° C., a slurry suitable for use in the spray drying can not be easily prepared due to the fact that the solubility of the compounds containing the constituent elements of the catalyst decreases and, therefore, the size of the fine particles obtained from the spray drying varies widely from particle to particle. On the other hand, if the mixing temperature is higher than 70° C., not only are the particles likely to agglomerate with each other when the spray dried fine particles are calcined, but also (i) the average pore diameter of the catalyst obtained by the calcination tends to be out of the range specified hereinabove and (ii) the acrylonitrile yield unpreferably decreases.

If the pH of the slurry is more than 4, the properties of the slurry gradually become unsuitable for the spray drying as the pH increases, and the shape of the particles of the catalyst so prepared is deformed so that a catalyst having a poor attrition resistance is formed. The slurry concentration is generally within the range of from 15 to 35% by weight and, preferably, within the range of from 20 to 30% by weight. If the slurry concentration is too low, a large amount of heat energy is unpreferably required for vaporizing a large amount of water from the slurry. On the other hand, if the slurry concentration is too high, the slurry becomes unsuitable for the spray drying.

The slurry is preferably aged, with stirring, for 1 to 30 hours (more preferably, 2 to 10 hours), under the conditions of a temperature of 30° to 70° C. (more preferably, 40° to 60° C.) and a pH of not more than 4 (more preferably, not more than 2). The pH can be easily adjusted by using, for example, nitric acid, aqueous ammonia or the like. The spray drying of the slurry can be carried out by using a hot gas (e.g. air) of 200° to 400° C. (preferably 250° to 350° C.), according to the conventional manner, in any conventional equipments such as a rotary disc type spray drier, a nozzle type spray dryer or the like. Thus, fine catalyst particles having an average size of, preferably, 40 to 80 microns and, more preferably 50 to 70 microns can be obtained.

As mentioned hereinabove, the spray dried fine particles thus obtained from the slurry are then calcined under an atmosphere of an oxygen-containing gas (generally in air), at a temperature of 500° to 700° C. (preferably 550° to 650° C.). If the calcination temperature is too low, the selectivity to the acrylonitrile unpreferably decreases. If the calcination temperature is too high, the conversion of the propylene unpreferably decreases.

One example of the preferred embodiments of the preparation process of the catalyst of the present invention is more specifically illustrated hereinbelow.

(A) A given amount of ammonium molybdate is dissolved in a given amount of warm water. Thus a solution (A) having a predetermined temperature is prepared.

(B) Given amounts of ferric nitrate and potassium are dissolved in a given amount of warm water. Thus, a solution (B) having a predetermined temperature is obtained.

(C) Given amounts of bismuth nitrate and zirconium oxide nitrate are dissolved in a given amount of dilute nitric acid. Thus, a solution (C) having a predetermined temperature is obtained.

(D) A given amount of silica sol (D) is kept at a predetermined temperature.

A slurry having a pH of not more than 4 (preferably, not more than 2) is prepared by mixing the liquids (A), (B), (C) and (D) at a temperature of 30° to 70° C. (preferably, 40° to 60° C.). As mentioned above, although the order in which the liquids (A), (B), (C) and (D) are added to each other is not specifically critical, it is preferable to add the liquid (D) to a mixed slurry of the liquids (A), (B) and (C) each having a pH of not more than 4 (preferably, not more than 2) or to a solution of the liquids (B) and/or (C) each having a pH of not more than 4 (preferably, not more than 2). The pH adjustment is optionally carried out by using, for example, nitric acid, aqueous ammonia or the like.

The slurry obtained by mixing the liquids (A), (B), (C) and (D) together is kept at the above-mentioned temperature range and pH range and, then, is spray-dried according to any conventional manner. Thus, fine particles having the desired size are obtained. The spray dried fine particles are then calcined under an atmosphere of an oxygen-containing gas at a temperature of 500° to 700° C. (preferably, 550° to 650° C.). Thus, the desired catalyst having micro pores on the surface thereof and comprising molybdenum, cobalt, bismuth, zirconium, potassium and oxygen supported on the silica carrier is obtained.

Then the catalytic ammoxidation of propylene is carried out by using the catalyst of the present invention in a fluidized bed reactor, the reaction temperature is generally within the range of from 380° to 500° C. and, preferably, from 410° to 470° C. The reaction is generally carried out under normal atmospheric pressure, but can also be carried out under slight pressure. The contact time is generally 1 to 10 seconds and, preferably, 3 to 6 seconds. Propylene, oxygen and ammonia are fed, as a raw feed, to the reactor in amounts of 1 to 4 moles (preferably 1.5 to 3 moles) of oxygen and 0.5 to 2 moles (preferably 0.8 to 1.2 moles) of ammonia, based on 1 mole of propylene. It is not necessary to use propylene, oxygen and ammonia which have a high purity as the raw materials. Although pure oxygen diluted with nitrogen is used as the starting oxygen, the use of air is preferable from an economical point of view. Steam, which is usually added to the gaseous raw materials when the catalytic ammoxidation of propylene is carried out in a fixed bed reactor, is not necessarily added in the above-mentioned fluidized bed reactor process. However, the addition of steam to the gaseous raw feed in the fluidized bed reactor process is preferable due to the fact that the selectivity to the desired acrylonitrile increases.

The particle size of the catalyst for the production of acrylonitrile according to the present invention is within the range of from 40 to 80 microns and, preferably 50 to 70 microns, and the problems of the conventional catalyst used in a fluidized bed reactor are remarkably improved by the catalyst of the present invention.

THE EXAMPLES

The present invention now will be further illustrated by, but by no means limited to, the following Examples together with Comparative Examples.

In the Examples and the Comparative Examples, the conversion (%) of the propylene, the selectivity (%) to the acrylonitrile and the acrylonitrile yield (%) are determined by the following equations.

$$\text{Conversion (\%) of Propylene} = \frac{\text{Moles of Propylene Consumed}}{\text{Moles of Propylene Fed}} \times 100$$

$$\text{Selectivity (\%) to Acrylonitrile} = \frac{\text{Moles of Acrylonitrile Formed}}{\text{Moles of Propylene Consumed}} \times 100$$

$$\text{Acrylonitrile Yield (\%)} = \frac{\text{Moles of Acrylonitrile Formed}}{\text{Moles of Propylene Fed}} \times 100$$

The average pore radius (Å) and the total pore volume (cm³/g) were measured by using a mercury pressure porosimeter (made from Carlo Erba Co.) method. The specific surface area (m²/g) was determined, according to the BET method based on nitrogen gas adsorption, by using a specific surface area measuring apparatus (made from Yuasa Battery Co.).

The attrition loss (%) in each Example was determined according to the Test Method For Synthetic Cracking Catalysts stated in American Cyanamide Co., 6/31-4m-1/57, which is well known as a test method for fluid catalytic cracking catalysts.

$$\text{Attrition Loss (\%)} = B/(C-A) \times 100$$

where A is an amount (g) of the catalyst which is lost by attrition between 0 and 5 hours; B is an amount (g) of the catalyst which is lost by attrition between 5 and 20 hours and C is an amount (g) of the catalyst which is used in the test. C was 50 g in each Example.

EXAMPLE 1

592.3 g of ammonium molybdate [$(NH_4)_6 \cdot Mo_7O_{24} \cdot 4H_2O$] was dissolved in 966 ml of warm water at a temperature of approximately 50° C. The resultant solution liquid (A) was kept at a temperature of approximately 50° C.

585.8 g of cobalt nitrate [$Co(NO_3)_2 \cdot 6H_2O$], 135.5 g of ferric nitrate [$Fe(NO_3)_3 \cdot 9H_2O$] and 2.375 g of potassium nitrate ($KNO_3$) were dissolved in 643 ml of warm water at a temperature of approximately 50° C. The resultant solution (liquid B) was kept at a temperature of approximately 50° C.

162.7 g of bismuth nitrate [$Bi(NO_3)_3 \cdot 5H_2O$] and 22.42 g of zirconium oxide nitrate [$ZrO(NO_3)_2 \cdot 2H_2O$] was dissolved in dilute nitric acid, which was previously prepared by mixing 487 ml of water and 90 ml of 60% nitric acid, at a temperature of 50° C. The resultant solution (liquid C) was kept at a temperature of approximately 50° C.

2500 g of silica sol containing 30% by weight of $SiO_2$ was heated and kept at a temperature of approximately 50° C. (liquid D).

The resultant liquids B and C are mixed with each other at the above-mentioned temperature. The mixed solution thus obtained was then dropwise added to the solution A while stirring. Thus, the mixed solution, consisting of the liquids A, B and C having a pH of not more than 1, was prepared. Thereafter, the liquid D was added to the resultant mixed solution and the mixture was aged while stirring for 2 hours at a temperature of approximately 50° C. Thus, the slurry having a pH of not more than 1 and a temperature of approximately 50° C. was prepared.

While the pH and the temperature of the slurry was kept constant, the slurry was homogenized by using a homogenizer and, then, was spray dried, in a conventional manner, by using a rotary disc type spray drier. The spray dried fine particles were dried for 16 hours at a temperature of 230° C. and were, then, calcined under air atmosphere in a calcination furnace. The fine particles were heated at a heating rate of 100° C./hr and calcined for 10 hours at 600° C. Thus, catalyst particles having an average size of 60 microns and having pores on the surface thereof were obtained.

The composition of the catalyst was $Mo_{10} Co_6 Fe_1 Bi_1 Zr_{0.25} K_{0.07}$ (oxygen has not been mentioned here even though it is present) and 50% by weight of silica, in terms of $SiO_2$, was contained in the catalyst. The average pore radius, the total pore volume and the specific surface area of the catalyst are shown in Table 1 below.

150 ml of the catalyst prepared above was charged into a fluidized bed reactor having an inner diameter of 36 mm. The ammoxidation reaction was then carried out by feeding 1922.2 ml/min of a mixed gas of propylene, ammonia, air and steam in an amount (mole ratio) of 1:1.14:12.06:1, respectively. The contact time was 4.68 seconds and the reaction temperature was 440° C.

The results of the ammoxidation reaction and the attrition loss of the catalyst are shown in Table 2 below.

EXAMPLE 2 THROUGH 6

The catalysts were prepared in a similar manner to that described in Example 1, except that the following changes were made: In Examples 2 and 3, the temperatures of the preparation of the mixed solutions and the slurry were 40° C. and 60° C., respectively. In Example 4, the amount of the silica sol used in the preparation was such an amount that the silica content, in terms of $SiO_2$, in the catalyst was 45% by weight. In Examples 5 and 6, the calcinations temperatures were 560° C. and 650° C., respectively. The average radius, the total pore volume and the specific surface area of the catalysts are shown in Tables 1 and 2 below.

The ammoxidation reactions were carried out by using the catalysts thus obtained in a manner similar to that described in Example 1. The results are shown in Table 2 below.

EXAMPLE 7

The catalyst was prepared in a similar manner to that described in Example 1, except that the liquid D was first added to the mixture of the liquids B and C, followed by the dropwise addition of the liquid A. The properties of the catalyst thus obtained are shown in Table 1 below.

The ammoxidation reaction was carried out by using the catalyst thus prepared in a manner similar to that described in Example 1. The results are shown in Table 2 below.

TABLE 1

| Example No. | Catalyst Composition (Atomic Ratio*[1]) | $SiO_2$ Content*[2] (wt.%) | Slurry Preparation Temperature (°C.) | Calcination Temperature (°C.) | Average Pore Radius (Å) | Total Pore Volume (cm³/g) | Specific Surface Area (m²/g) |
|---|---|---|---|---|---|---|---|
| 1 | $Mo_{10}Co_6Fe_1Bi_1Zr_{0.25}K_{0.07}$ | 50 | 50 | 600 | 254 | 0.357 | 49.3 |

TABLE 1-continued

| Example No. | Catalyst Composition (Atomic Ratio*[1]) | SiO$_2$ Content*[2] (wt.%) | Slurry Preparation Temperature (°C.) | Calcination Temperature (°C.) | Average Pore Radius (Å) | Total Pore Volume (cm$^3$/g) | Specific Surface Area (m$^2$/g) |
| --- | --- | --- | --- | --- | --- | --- | --- |
| 2 | " | 50 | 40 | 600 | 251 | 0.335 | 53.2 |
| 3 | " | 50 | 60 | 600 | 247 | 0.370 | 46.5 |
| 4 | " | 45 | 50 | 600 | 293 | 0.375 | 43.5 |
| 5 | " | 50 | 50 | 560 | 232 | 0.311 | 56.2 |
| 6 | " | 50 | 50 | 650 | 275 | 0.421 | 45.6 |
| 7 | " | 50 | 50 | 600 | 239 | 0.380 | 53.5 |

*[1]Oxygen has not been mentioned here even though it is present.
*[2]Silica content in the catalyst interms of SiO$_2$.

TABLE 2

| Example No. | Propylene Conversion (%) | Selectivity to Acrylonitrile (%) | Acrylonitrile Yield (%) | Attrition Loss (%) |
| --- | --- | --- | --- | --- |
| 1 | 97.4 | 85.4 | 83.2 | 0.35 |
| 2 | 97.2 | 85.5 | 83.1 | 0.97 |
| 3 | 97.0 | 85.5 | 82.9 | 1.41 |
| 4 | 97.2 | 86.1 | 83.7 | 1.40 |
| 5 | 99.0 | 81.3 | 80.5 | 1.20 |
| 6 | 93.0 | 87.1 | 81.0 | 0.80 |
| 7 | 98.1 | 84.6 | 83.0 | 0.44 |

EXAMPLES 8 THROUGH 12

The catalysts having the compositions shown in Table 3 below and containing 50% by weight of silica (in terms of SiO$_2$) were prepared in a similar manner to that described in Example 1, except that the amounts of ferric nitrate, cobalt nitrate, bismuth nitrate, zirconium oxide nitrate and potassium nitrate were changed. The properties of the catalysts thus obtained are shown in Table 3 below.

The ammoxidation reactions were carried out by using the catalysts thus prepared in a manner similar to that described in Example 1. The results are shown in Table 4 below.

EXAMPLE 13

The catalyst having pores on the surface thereof and containing 50% by weight of silica (in terms of SiO$_2$) was prepared in a similar manner to that described in Example 1, except that a solution having a temperature of 50° C. prepared by dissolving 390.6 g of cobalt nitrate, 195.2 g of nickel nitrate [Ni(NO$_3$)$_2$.6H$_2$O], 135.5 g of ferric nitrate and 2.375 g of potassium nitrate into 643 ml of warm water at a temperature of approximately 50° C. was used as the liquid B. The properties of the catalyst thus prepared are shown in Table 3.

The ammoxidation reaction was carried out by using the catalyst thus prepared in a manner similar to that described in Example 1. The results are shown in Table 4 below.

TABLE 3

| Example No. | Catalyst Composition (Atomic Ratio*[1]) | Average Pore Radius (Å) | Total Pore Volume (cm$^3$/g) | Specific Surface Area (m$^2$/g) |
| --- | --- | --- | --- | --- |
| 8 | Mo$_{10}$Co$_6$Fe$_3$Bi$_1$Zr$_{0.25}$K$_{0.07}$ | 253 | 0.360 | 46.7 |
| 9 | Mo$_{10}$Co$_{6.5}$Fe$_{0.5}$Bi$_1$Zr$_{0.25}$K$_{0.07}$ | 264 | 0.356 | 46.3 |
| 10 | Mo$_{10}$Co$_6$Fe$_1$Bi$_{0.5}$Zr$_{0.25}$K$_{0.07}$ | 253 | 0.339 | 46.9 |
| 11 | Mo$_{10}$Co$_6$Fe$_1$Bi$_1$Zr$_{0.5}$K$_{0.07}$ | 264 | 0.360 | 47.1 |
| 12 | Mo$_{10}$Co$_6$Fe$_1$Bi$_1$Zr$_{0.25}$K$_{0.03}$ | 246 | 0.346 | 48.6 |
| 13 | Mo$_{10}$Co$_4$Ni$_2$Fe$_1$Bi$_1$Zr$_{0.25}$K$_{0.07}$ | 222 | 0.342 | 47.6 |

*[1]See Table 1

TABLE 4

| Example No. | Propylene Conversion (%) | Selectivity to Acrylonitrile (%) | Acrylonitrile Yield (%) | Attrition Loss (%) |
| --- | --- | --- | --- | --- |
| 8 | 93.3 | 86.2 | 80.4 | 0.79 |
| 9 | 95.2 | 86.8 | 82.6 | 1.75 |
| 10 | 98.0 | 84.1 | 82.4 | 0.45 |
| 11 | 97.7 | 86.0 | 84.0 | 0.97 |
| 12 | 97.6 | 82.0 | 80.0 | 0.45 |
| 13 | 98.0 | 83.8 | 82.1 | 0.86 |

EXAMPLE 14 THROUGH 17

The catalysts having the compositions shown in Table 5 below and containing 50% by weight of silica (in terms of SiO$_2$) were prepared in a similar manner to that described in Example 1, except that rubidium nitrate (RbNO$_3$) or cesium nitrate (CsNO$_3$) was used in a different amount instead of potassium nitrate in the liquid B. In addition, the silica sol was added in Example 15 in such as amount that 45% by weight of silica was contained in the catalyst. The properties of the catalyst thus prepared are shown in Table 5 below.

The ammoxidation reactions were carried out by using these catalysts in a manner similar to that described in Example 1. The results are shown in Table 6 below.

TABLE 5

| Example No. | Catalyst Composition (Atomic Ratio*[1]) | Average Pore Radius (Å) | Total Pore Volume (cm$^3$/g) | Specific Surface Area (m$^2$/g) |
| --- | --- | --- | --- | --- |
| 14 | Mo$_{10}$Co$_6$Fe$_1$Bi$_1$Zr$_{0.25}$Rb$_{0.05}$ | 256 | 0.349 | 48.5 |
| 15 | Mo$_{10}$Co$_6$Fe$_1$Bi$_1$Zr$_{0.25}$Rb$_{0.05}$ | 291 | 0.380 | 43.3 |
| 16 | Mo$_{10}$Co$_6$Fe$_1$Bi$_1$Zr$_{0.25}$Cs$_{0.03}$ | 255 | 0.354 | 48.9 |
| 17 | Mo$_{10}$Co$_6$Fe$_1$Bi$_1$Zr$_{0.25}$K$_{0.05}$Cs$_{0.08}$ | 257 | 0.356 | 49.1 |

*[1]See Table 1

TABLE 6

| Example No. | Propylene Conversion (%) | Selectivity to Acrylonitrile (%) | Acrylonitrile Yield (%) | Attrition Loss (%) |
| --- | --- | --- | --- | --- |
| 14 | 97.3 | 85.4 | 83.1 | 0.49 |
| 15 | 97.1 | 86.5 | 84.0 | 1.70 |
| 16 | 96.1 | 86.5 | 83.1 | 0.66 |
| 17 | 97.2 | 85.8 | 83.4 | 0.55 |

EXAMPLE 18 THROUGH 25

The catalysts having the compositions shown in Table 7 below and containing 50% by weight of silica, in terms of CiO$_2$, were prepared in a similar manner to that described in Example 1, except that titanium dioxide powder ($TiO_2$, rutile type), tellurium oxide powder ($TeO_2$), vanadium pentoxide powder ($V_2O_5$), manganese dioxide powder ($MnO_2$), chromium oxide ($Cr_2O_3$), ammonium paratangstate [$(NH_4)_{10}W_{12}O_{41} \cdot 5H_2O$] or stannic oxide powder ($SnO_2$) was used, as the liquid A, in such an amount that the compositions of the catalysts shown in Table 7 were obtained. The properties of the catalysts thus prepared are shown in Table 7 below.

The ammoxidation reactions were carried out in a manner similar to that described in Example 1. The results are shown in Table 8 below.

TABLE 7

| Example No. | Catalyst Composition (Atomic Ratio*[1]) | Average Pore Radius (Å) | Total Pore Volume (cm³/g) | Specific Surface Area (m²/g) |
|---|---|---|---|---|
| 18 | $Mo_{10}Co_6Fe_1Bi_1Zr_{0.25}K_{0.07}Ti_1$ | 269 | 0.352 | 47.1 |
| 19 | $Mo_{10}Co_6Fe_1Bi_1Zr_{0.25}K_{0.07}Ti_3$ | 265 | 0.343 | 50.6 |
| 20 | $Mo_{10}Co_6Fe_1Bi_1Zr_{0.25}K_{0.07}Te_{0.1}$ | 254 | 0.356 | 47.6 |
| 21 | $Mo_{10}Co_6Fe_1Bi_1Zr_{0.25}K_{0.07}V_{0.3}$ | 259 | 0.342 | 48.3 |
| 22 | $Mo_{10}Co_6Fe_1Bi_1Zr_{0.25}K_{0.07}Mn_{0.3}$ | 263 | 0.339 | 46.5 |
| 23 | $Mo_{10}Co_6Fe_1Bi_1Zr_{0.25}K_{0.07}Cr_{0.3}$ | 254 | 0.359 | 49.9 |
| 24 | $Mo_{10}Co_6Fe_1Bi_1Zr_{0.25}K_{0.07}W_{0.3}$ | 264 | 0.354 | 48.3 |
| 25 | $Mo_{10}Co_6Fe_1Bi_1Zr_{0.25}K_{0.07}Sn_{0.3}$ | 258 | 0.372 | 48.2 |

*[1] See Table 1

TABLE 8

| Example No. | Propylene Conversion (%) | Selectivity to Acrylonitrile (%) | Acrylonitrile Yield (%) | Attrition Loss (%) |
|---|---|---|---|---|
| 18 | 97.0 | 87.5 | 84.9 | 1.46 |
| 19 | 96.0 | 87.0 | 83.5 | 1.75 |
| 20 | 97.5 | 85.5 | 83.4 | 0.63 |
| 21 | 98.0 | 85.9 | 84.2 | 0.92 |
| 22 | 97.6 | 86.6 | 84.5 | 1.32 |
| 23 | 98.1 | 85.3 | 83.7 | 1.10 |
| 24 | 97.3 | 86.4 | 84.1 | 0.75 |
| 25 | 96.9 | 86.1 | 83.4 | 0.60 |

COMPARATIVE EXAMPLES 1 THROUGH 5

The catalysts were prepared in a manner similar to that described in Example 1, except that the following changes were made.

Comparative Example 1: the preparation temperatures of the mixed solution and the slurry was changed to 80° C.

Comparative Example 2: the pH of the slurry was adjusted to 5 by the addition of aqueous ammonia during the slurry preparation.

Comparative Examples 3 and 4: the silica sol was used in such an amount that 35% by weight and 65% by weight of silica, in terms of $SiO_2$, was contained in the catalyst, respectively.

Comparative Example 5: the calcination temperature was changed to 450° C.

The compositions and the preparation conditions are shown in Table 9 below. The properties of the catalysts are shown in Table 10 below.

COMPARATIVE EXAMPLES 6 THROUGH 12

The catalysts having the compositions shown in Table 9 below (which compositions are out of the range of the present invention) were prepared in a similar manner to that described in Example 1, except that the amounts of cobalt nitrate, ferric nitrate, bismuth nitrate, potassium and the like were changed or zirconium oxide nitrate was not used. The properties of the catalyst thus obtained are shown in Table 10 below.

The ammoxidation reactions were carried out by using the catalysts obtained above in a manner similar to that described in Example 1. The results are shown in Table 10 below.

TABLE 9

| Comparative Example No. | Catalyst Composition (Atomic Ratio*[1]) | | | | | | $SiO_2$ Content (wt. %) | Slurry Preparation | | Calcination Temp. (°C.) |
|---|---|---|---|---|---|---|---|---|---|---|
| | Mo | Co | Fe | Bi | Zr | K | | Temp. (°C.) | pH | |
| 1 | 10 | 6 | 1 | 1 | 0.25 | 0.07 | 50 | 80 | ≦1 | 600 |
| 2 | 10 | 6 | 1 | 1 | 0.25 | 0.07 | 50 | 50 | ≦5 | 600 |
| 3 | 10 | 6 | 1 | 1 | 0.25 | 0.07 | 35 | 50 | ≦1 | 600 |
| 4 | 10 | 6 | 1 | 1 | 0.25 | 0.07 | 65 | 50 | ≦1 | 600 |
| 5 | 10 | 6 | 1 | 1 | 0.25 | 0.07 | 50 | 50 | ≦1 | 450 |
| 6 | 10 | 10 | 1 | 1 | 0.25 | 0.07 | 50 | 50 | ≦1 | 600 |
| 7 | 10 | 1 | 1 | 1 | 0.25 | 0.07 | 50 | 50 | ≦1 | 600 |
| 8 | 10 | 6 | 8 | 1 | 0.25 | 0.07 | 50 | 50 | ≦1 | 600 |
| 9 | 10 | 6 | 0.05 | 1 | 0.25 | 0.07 | 50 | 50 | ≦1 | 600 |
| 10 | 10 | 6 | 1 | 4 | 0.25 | 0.07 | 50 | 50 | ≦1 | 600 |
| 11 | 10 | 6 | 1 | 1 | 0 | 0.07 | 50 | 50 | ≦1 | 600 |
| 12 | 10 | 6 | 1 | 1 | 0.25 | 2 | 50 | 50 | ≦1 | 600 |

*[1] See Table 1

TABLE 10

| Comparative Example No. | Average Pore Radius (Å) | Total Pore Volume (cm³/g) | Specific Surface Area (m²/g) | Propylene Conversion (%) | Selectivity to Acrylonitrile (%) | Acrylonitrile Yield (%) | Attrition Loss (%) |
|---|---|---|---|---|---|---|---|
| 1 | 146 | 0.357 | 39.9 | 89.7 | 79.0 | 70.9 | 1.50 |
| 2 | 240 | 0.516 | 42.5 | 95.4 | 84.0 | 80.1 | 10 |
| 3 | 256 | 0.560 | 34.9 | 96.3 | 86.9 | 83.7 | 10 |
| 4 | 125 | 0.198 | 63.5 | 90.6 | 76.5 | 69.3 | 0.38 |
| 5 | 293 | 0.495 | 63.2 | 99.6 | 73.0 | 72.7 | 7.20 |
| 6 | 325 | 0.476 | 50.6 | 98.3 | 76.9 | 75.6 | 9.20 |
| 7 | 256 | 0.340 | 50.9 | 84.5 | 80.6 | 68.1 | 2.43 |

TABLE 10-continued

| Comparative Example No. | Average Pore Radius (Å) | Total Pore Volume (cm³/g) | Specific Surface Area (m²/g) | Propylene Conversion (%) | Selectivity to Acrylonitrile (%) | Acrylonitrile Yield (%) | Attrition Loss (%) |
| --- | --- | --- | --- | --- | --- | --- | --- |
| 8 | 269 | 0.401 | 43.6 | 87.3 | 79.2 | 69.1 | 0.42 |
| 9 | 239 | 0.335 | 49.1 | 89.4 | 74.9 | 67.0 | 1.70 |
| 10 | 315 | 0.513 | 46.9 | 92.0 | 78.0 | 71.8 | 7.60 |
| 11 | 256 | 0.352 | 49.6 | 93.0 | 78.3 | 72.8 | 0.98 |
| 12 | 246 | 0.341 | 46.5 | 80.6 | 86.9 | 70.0 | 3.40 |

What we claim is:

1. In a catalyst containing molybdenum, cobalt, iron, bismuth, zirconium, the alkali metals and oxygen supported on a carrier which is used for producing acrylonitrile by the catalytic ammoxidation of propylene in a fluidized bed reactor; the improvement wherein the catalyst comprises 40 to 60% by weight, in terms of $SiO_2$, of silica and 60 to 40% by weight of an oxide composition having the formula [I]:

$$Mo_a Co_b Ni_c Fe_d Bi_e Zr_f A_g X_h O_j \quad [I]$$

wherein Mo is molybdenium, Co is cobalt, Ni is nickel, Fe is iron, Bi is bismuth, Zr is zirconium, A is the alkali metals, X is at least one element selected from the group consisting of titanium, tellurium, vanadium, manganese, chromium, tungsten and tin and O is oxygen; the subscripts a, b, c, d, e, f, g, h and j represent the number of atoms in the catalyst and, when a is 10, b is 2 to 8 and c is 0 to 8 provided that b+c is 2 to 10, d is 0.1 to 7, e is 0.1 to 3, f is 0.1 to 4, g is 0.01 to 1, h is 0 to 5 and j is a number which is required by the total valence of the other elements except for oxygen and is generally 32.5 to 78.5, and has micro pores on the surface thereof, the average pore radius being 150 to 500 Å and the total pore volume being 0.2 to 0.5 cm³/g and the specific surface area of the catalyst being 30 to 60 m²/g.

2. The catalyst as claimed in claim 1, wherein said alkali metal A in the formula is at least one alkali metal selected from the group consisting of potassium, rubidium and cesium.

3. The catalyst as claimed in claim 1, wherein said catalyst is prepared by the steps of:
   (i) mixing silica sol and compounds containing the constituent elements of formula [I] wich each other in an aqueous medium at a temperature of 30° to 70° C. to thereby form a slurry having a pH of not more than 4,
   (ii) spray drying the slurry to form fine particles; and
   (iii) calcinating the spray dried particles at a temperature of 500° to 700° C.

4. The catalyst as claimed in claim 3, wherein said slurry has a concentration of 15 to 35% by weight and said slurry is aged for 1 to 30 hours at a temperature of 30° to 70° C.

5. The catalyst as claimed in claim 3, wherein said fine particles have an average size of 40 to 80 microns.

* * * * *

UNITED STATES PATENT AND TRADEMARK OFFICE
CERTIFICATE OF CORRECTION

PATENT NO. : 4,264,476
DATED : April 28, 1981
INVENTOR(S) : Sumio Umeura et al

It is certified that error appears in the above-identified patent and that said Letters Patent are hereby corrected as shown below:

Table 9, Examples 1-12, column 12, delete "$<$" and insert -- $\leq$ --.

Signed and Sealed this

Twenty-third Day of March 1982

|SEAL|

Attest:

Attesting Officer

GERALD J. MOSSINGHOFF

Commissioner of Patents and Trademarks